(12) United States Patent
Chaplin et al.

(10) Patent No.: US 7,358,236 B1
(45) Date of Patent: Apr. 15, 2008

(54) CONTROL OF ACUTE HYPERTENSION AND CARDIOTOXICITY IN PATIENTS TREATED WITH VASCULAR TARGETING AGENTS

(75) Inventors: David Chaplin, Watlington (GB); Scott Young, Stowe, MA (US)

(73) Assignee: OXiGENE, Inc., Waltham, MA (US)

( * ) Notice: Subject to any disclaimer, the term of this patent is extended or adjusted under 35 U.S.C. 154(b) by 515 days.

(21) Appl. No.: 10/602,325

(22) Filed: Jun. 23, 2003

Related U.S. Application Data (60) Provisional application No. 60/390,727, filed on Jun. 21, 2002.

(51) Int. Cl.
 *A61K 31/66* (2006.01)
 *A61K 31/075* (2006.01)
(52) U.S. Cl. .................................. 514/130; 514/720
(58) Field of Classification Search .................... None
 See application file for complete search history.

(56) References Cited

U.S. PATENT DOCUMENTS

| | | | | |
|---|---|---|---|---|
| 4,996,237 | A * | 2/1991 | Pettit et al. | 514/720 |
| 5,561,122 | A * | 10/1996 | Pettit | 514/130 |
| 6,538,038 | B1 * | 3/2003 | Pero et al. | 514/731 |
| 6,720,323 | B2 * | 4/2004 | Arnould | 514/237.5 |
| 6,773,702 | B2 * | 8/2004 | Pero et al. | 424/93.21 |
| 7,091,240 | B2 * | 8/2006 | Pinney et al. | 514/469 |
| 2003/0144298 | A1 * | 7/2003 | Curwen et al. | 514/252.17 |

FOREIGN PATENT DOCUMENTS

| WO | WO 9935150 A1 * | 7/1999 |
|---|---|---|
| WO | WO01/74360 | 10/2001 |

OTHER PUBLICATIONS

Cecil Textbook of Medicine, 20th Edition, Bennet et al., 1997.*
Dowlati, et al., "A Phase I Pharmacokinetic and Translational Study of the Novel Vascular Targeting Agent Combretastatin A-4 Phosphate on a Single-Dose Intravenous Schedule in Patients with Advanced Cancer", *Cancer Res.*, 62:3408-3416 (2002).
Honess, et al., "Comparison of Strategies to Overcome the Hypertensive Effect of Combretastatin-A-4 Phosphate in a Rat Model", *British J. Cancer*, 86(Suppl. I):S118-S119 (2002).
Prise, et al., "The Vascular Response of Tumor and Normal Tissues in the Rat to the Vascular Targeting Agent, Combretastatin A-4-Phosphate, at Clinically Relevant Doses", *Int'l J. Oncology*, 21:717-726 (2002).
Tozer, et al., "Combretastatin A-4 Phosphate as a Tumor Vascular-Targeting Agent: Early Effects in Tumors and Normal Tissues", *Cancer Res.*, 59:1626-1634 (1999).

* cited by examiner

*Primary Examiner*—Brian Kwon
(74) *Attorney, Agent, or Firm*—Ivor R. Elrifi; Naomi S. Biswas; Mintz, Levin, Cohn, Ferris, Glovsky and Popeo, P.C.

(57) ABSTRACT

The present invention provides a method of using antihypertensive agents ("AHAs") to attenuate the transient increase in blood pressure observed in patients where Vascular Targeting Agents ("VTAs") are administered to treat diseases associated with malignant neovascularization. The invention also relates to pharmaceutical compositions comprising AHAs and VTAs, and to kits thereof.

13 Claims, 3 Drawing Sheets

CONTROL OF ACUTE HYPERTENSION AND CARDIOTOXICITY IN PATIENTS TREATED WITH VASCULAR TARGETING AGENTS

RELATED APPLICATIONS

This application claims the benefit of U.S. Ser. No. 60/390,727, filed Jun. 21, 2002, the contents of which are incorporated by reference in their entirety.

BACKGROUND OF THE INVENTION

Cancer is a leading cause of death in the industrialized world and despite years of research many types of cancer lack an effective therapeutic treatment. This is especially true for cancers that are characterized by the presence of large, solid tumors since it is difficult to deliver an effective dose of a chemotherapeutic agent to the interior of a large tumor mass with a degree of selectivity. Moreover, due to the genetic instability of tumor cells, a tumor tissue can rapidly acquire resistance to standard therapeutic regimens.

In order to develop into a large solid tumor mass however, a tumor foci must first establish a network of blood vessels in order to obtain the nutrients and oxygen required for further growth. This tumor-induced vasculature has received enormous interest as a target for antineoplastic therapy because a relatively small number of blood vessels are critical for the survival and continued growth of a much larger group of cancer cells. The disruption in the function of a single tumor blood vessel can result in an avalanche of ischaemic cell death and necrosis of thousands of tumor cells which depend on it for blood supply. In addition, the accessibility of the tumor vasculature by blood-borne antivascular therapeutics and the relatively stable genome of normal host vascular tissue can alleviate some of the problems of bioavailability and acquired drug resistance that plague conventional, anti-tumor based therapies.

Much of the research in anti-vascular cancer therapy has focused on understanding the process of new blood vessel formation or "angiogenesis" and identifying anti-angiogenic agents which inhibit the formation of new blood vessels. Angiogenesis is characterized by the proliferation of tumor endothelial cells and generation of new vasculature to support the growth of a tumor. This growth is stimulated by several growth factors produced by the tumor itself. One of these growth factors, Vascular Endothelial Growth Factor ("VEGF"), is relatively specific towards endothelial cells, by virtue of the restricted and up-regulated expression of its cognate receptor. Various anti-angiogenic strategies have been developed to inhibit this signaling process at one or more steps in the biochemical pathway in order to prevent the growth and establishment of the tumor vasculature. However, anti-angiogenic therapies act slowly and must be chronically administered to produce a desired effect.

Vascular Targeting Agents ("VTAs"), also known as Vascular Damaging Agents, are a novel class of antineoplastic drugs which attack solid tumors by selectively destroying the existing vasculature formed by angiogenesis. The cytotoxic mechanism of VTA action is quite divorced from that of anti-angiogenic agents. A single dose of VTA can cause a rapid and irreversible tumor vascular shutdown of existing tumor vasculature, leading eventually to tumor necrosis by induction of hypoxia and nutrient depletion. Other agents have been known to disrupt tumor vasculature but differ in that they also manifest substantial normal tissue toxicity at their maximum tolerated dose. In contrast, genuine VTAs retain their vascular shutdown activity at a fraction of their maximum tolerated dose.

Combretastatin A-4 Disodium Phosphate Prodrug ("CA-4DP") is the lead drug of a group of VTAs currently in clinical trials as a VTA. This compound was initially isolated as Combretastatin A-4 ("CA-4") from the stem wood of the African tree *Combretum caffrum* (Combretaceae). As described in U.S. Pat. No. 4,996,237, the entire disclosure of which is incorporated herein in entirety, CA-4 was synthesized and found to have tubulin binding activity. Moreover, CA-4 was found to be a potent inhibitor of microtubule assembly in tumor endothelium. However, due to the insolubility of CA-4 in human plasma, CA-4DP was developed and found to have superior activity as a VTA (U.S. Pat. No. 5,561,122, the entire disclosure of which is incorporated by reference). When administered to the bloodstream of a patient, the CA-4DP is cleaved to the active, tubulin-binding CA-4 by endogenous nonspecific phosphatases. It is thought that CA-4 selectively destabilizes the microtubule cytoskeleton of tumor endothelial cells, causing a profound alteration in the shape of the cell which ultimately leads to occlusion of the tumor blood vessel and shutdown of blood flow to the tumor (Kanthou and Tozer, Blood, 2002, 99(6): 2060-2069).

In vivo studies have confirmed that vascular damaging affects of CA-4P on tumor tissue far exceed its effects on normal tissues. While a dosage of 100 mg/kg can cause a 100-fold reduction in the tumor blood flow of a rat, blood flow is maintained at normal levels in vital tissues such as the heart, kidney, or small intestine (Tozer et al. Cancer Research, 1999, 59: 1626-1634, incorporated herein by reference). However, these studies did observe a substantial but transient increase in Mean Arterial Blood Pressure ("MABP") in peripheral tissues, almost immediately following administration of CA-4P. The risks of VTA-induced hypertension are significant and may have life-threatening consequences, especially for human cancer patients who are burdened with an additional cardiac disorder. The complications associated with untreated drug-induced hypertension can include chest pains (angina pectoris), nausea, and headaches and may ultimately lead to tachychardia, congestive heart failure, kidney damage, stroke, loss of vision, or a myocardial infarction (heart attack) due to ischemia or lack of oxygen in the heart tissue.

It has been reported that anti-angiogenic agents can also cause an increase in blood pressure. In contrast with the acute and transient nature of the VTA-induced hypertension, this hypertension leads to a sustained increase in blood pressure that lasts for several weeks. International patent publication WO 01/74360 teaches a method for treating the chronic hypertension that is associated with administration of the VEGF Receptor Tyrosine Kinase ("RTK") inhibitor 4-(4-bromo-2-fluoroanilino)-6-methoxy-7-(1-methylpiperidin-4-ylmethoxy) quinazoline. The method comprises continuous dosing of the VEGF RTK inhibitor for several days followed by chronic administration of the Angiotensin Converting Enzyme ("ACE") inhibitor Captopril. We have found that an antihypertensive agent is also effective in controlling the transient increase in blood pressure that is associated with a single dose of a VTA, and that, surprisingly, co-administration of a VTA and an anti-hypertensive does not compromise the desired tumor blood flow shutdown effect of the VTA.

Another surprising observation of the present invention is that while a single dose of CA-4P can cause minor cardiotoxicity within 24 hrs of treatment these symptoms appear to be reversible. Chemotherapy-induced cardiotoxicity has been a major problem with several other cancer therapies but is associated with long-term additive effects of cumulative doses of conventional cytotoxic agents over the period of months or years following initial treatment. Of the conventional chemotherapeutic drugs, anthracyclines are the most widely recognized as causing cardiac complications. These complications include cardiomyopathy, myocarditis, congestive heart failure, pericarditis, arrhythmia which are chronic symptoms associated with long term effect of cumulative dosing of chemotherapeutic agents on the order of weeks, months or years. These cardiotoxic effects are irreversible and progressive and must be treated with long-term medication. In fact, for some drugs, there is an established lifetime maximum for which a drug can be taken.

The prior art has suggested the use of antihypertensive agents for the treatment of symptomatic heart failure prior to or following long-term, cumulative dosing with anthracycline-type antineoplastic agents (Simbre et al., Current Treatment Options in Cardiovascular Medicine, 2001, 3: 493-505; Sacco et al., Eur J of Pharmacology, 2001, 414: 71-8.) but does not suggest the unexpected result that antihypertensive agents can protect the acute and transient cardiotoxicity that is associated with the VTA-induced shutdown of blood supply to a tumor.

SUMMARY OF THE INVENTION

The invention involves a method of treatment of a disease-state associated with Vascular Targeting. A Vascular Targeting Agent and an Anti-Hypertensive Agent are administered to a mammal.

Vascular targeting agents are anti-angiogenic agents. Anti-angiogenic agents inhibit the growth and maintenance of new blood vessels. Other categories of anti-angiogenic agents include, agents which inhibit the action of growth factors and anti-invasive agents.

Vascular Targeting Agents include tubulin binding agents. Specific examples of vascular targeting agents are Combretastatins, Combretastatin analogs, and pharmaceutically acceptable salts thereof, such as Combretastatin A-4 Phosphate and Combretastatin A-1 Diphosphate.

Anti-hypertensive agents lower blood pressure. There are many different categories of anti-hypertensive agents including calcium channel blockers, angiotensin converting enzyme inhibitors (ACE inhibitors), angiotensin II receptor antagonists (A-II antagonists), diuretics, beta-adrenergic receptor blockers (beta-blockers), vasodilators, and alpha-adrenergic receptor blockers (alpha-blockers). One example of a beta-blocker is propranolol or a derivative thereof. One example of a vasodilator is Sodium Nitroprusside or a derivative thereof.

The invention also includes pharmaceutical compositions. The compositions include Vascular Targeting Agents or pharmaceutically acceptable salts or solvates thereof, Anti-Hypertensive Agents or pharmaceutically acceptable salts or solvates thereof, and optionally pharmaceutically acceptable carriers or diluents.

The invention further includes kits. The kits include Vascular Targeting Agents or pharmaceutically acceptable salts or solvates thereof or pharmaceutical compositions thereof, Anti-Hypertensive Agents or pharmaceutically acceptable salts or solvates thereof or pharmaceutical compositions thereof, and containers for containing these Agents.

Combinations of the invention are administered sequentially or simultaneously. When administered sequentially, either the anti-angiogenic agent or the anti-hypertensive agent can be administered first.

The invention additionally includes methods of manufacturing medicaments for the treatment of a disease state associated with Vascular Targeting in a mammal.

DETAILED DESCRIPTION OF THE INVENTION

The present invention provides a combination therapy that enables the safer use of Vascular Targeting Agents in a clinical setting. The combination provides an anti-hypertensive agent in conjunction with a VTA to attenuate any of the hypertensive effects of the VTA, to prevent the development of cardiotoxicity, or to otherwise alleviate sudden increases in blood pressure.

A conventional Beta-adrenergic blocking agent ("Beta blocker") is used as a prophylactic or interventional therapeutic agent to prevent or treat VTA-associated acute hypertension or cardiotoxicity in an animal patient. The preferred Beta blocker is propranolol hydrochloride which is available for use in clinical patients as oral or injectable formulations (Inderal®; Wyeth-Ayerst, Philadelphia, Pa.) or as a sustained-release capsule (Inderal®LA (Wyeth Ayerst, Philadelphia, Pa.). Other Beta blockers include oral formulations of Timolol Maleate (BLOCADREN®; Merck & Co., West Point, Pa.), Carteolol Hydrochloride (CARTROL®; Abbott Laboratories, Abbott Park, Ill.); Carvedilol (COREG®; SmithKline Beecham Pharmaceuticals, Philadelphia, Pa.), Betaxolol Hydrochloride (KERLONE®; G. D. Searle & Co., Chicago, Ill.), 1-(tert-butyl-amino)$_3$-[(5,6,7,8-tetrahydro-cis-6,7-dihydroxy-1-naphthyl)oxy]-2-propanolol (Nadolol; Mylan Pharmaceuticals Inc., Morgantown, W. Va.), Labetalol Hydrochloride (NORMODYNE®; Schering Corporation, Kenilworth, N.J.), Acebutolol Hydrochloride (SECTRAL®; Wyeth-Ayerst, Philadelphia, Pa.), Atenolol (TENORMIN®; AstraZeneca Pharmaceuticals, Wilmington, Del.), Metoprolol Succinate (TOPROL-XL®; AstraZeneca Pharmaceuticals, Wilmington, Del.), or Bisoprolol Fumarate (ZEBETA®; Lederle Pharmaceutical, Pearl River, N.Y.). Injectable formulations of Atenolol, Labetalol Hydrochloride, and Esmolol Hydrochloride (BREVIBLOC®; Baxter Pharmaceuticals, New Providence, N.J.) are also available.

In another embodiment of the invention, the inorganic rapid-acting vasodilator, Disodium Pentacyaanonitrosylferrate (2-)dihydrate (Sodium Nitroprusside; Baxter Pharmaceuticals) is used to prevent an adverse cardiac event in animal patients with VTA-associated acute hypertension or cardiotoxicity. Sodium Nitroprusside ("SNP") is supplied for human clinical use as an injectable formulation but must first be diluted in 5% dextrose before infusion. In humans, the drug should only be infused briefly or until the normal blood pressure is restored in order to prevent a precipitous decrease in blood pressure or cyanide toxicity. Other vasodilators include oral formulations of the coronary vasodilators Isosorbide mononitrate (ISMO®; Wyeth-Ayerst, Philadelphia, Pa.), Isosorbide Dinitrate, (ISOSORDIL®; Wyeth-Ayerst, Philadelphia, Pa.), or Nitroglycerin (NITROSTAT®; Parke-Davis, Morris Plains, N.J.). There are also injectable formulations of the peripheral vasodilators Fenoldopam Mesylate (CORLOPAM®; Abbott Laboratories, Abbott Park, Ill.), Epoprostenol sodium (FLOLAN®; Glaxo Wellcome, Research Triangle Park, N.C.) or Milrinone lactate (PRIMACOR®; Sanofi-Synthelabo, New York, N.Y.).

Other cardiovascular agents include alpha adrenergic blockers or alpha blockers, angiotensin converting enzyme (ACE) inhibitors, angiotensin II receptor antagonists, or calcium channel blockers.

In accordance with the present invention, the preferred VTA is CA-4DP, a disodium salt of the phosphate prodrug of CA-4 which has the following structure:

1, CA4DP

The invention is not limited in this respect, however, and other phosphate prodrug salts of CA-4 have been disclosed in published PCT applications WO 02/22626 and WO 99/35150.

Other Combretastatins that have been isolated, structurally elucidated, and synthesized can be used. U.S. Pat. Nos. 5,409,953, 5,569,786, and 4,490,726 describe the isolation and synthesis of Combretastatins designated as A-1, A-2, A-3, B-1, B-2, B-3, B-4, D-1, and D-2. Some of these compounds have been modified as phosphate prodrugs as disclosed in WO 01/8355. The disclosures of these references are incorporated herein in their entirety.

In a preferred embodiment, the Combretastatin is the diphosphate stilbene compound Combretastatin A-1 tetrasodium diphosphate prodrug ("CA1TP", 3) of Combretastatin A-1 ("CA-1", 2) which has the following structure:

2, CA1
3, CA1TP

Synthetic analogs of the Combretastatins are described in Pettit et al, Can. J. Chem., 1982; Pettit et al, J. Org. Chem., 1985; Pettit et al, J. Nat. Prod., 1987; Lin et al, Biochemistry, 1989; Singh et al, J. Org. Chem., 1989; Cushman et al, J. Med. Chem., 1991; Getahun et al, J. Med. Chem., 1992; Andres et al, Bioorg. Med. Chem. Lett., 1993; Mannila, Liebigs. Ann. Chem., 1993; Shirai et al, Bioorg. Med. Chem. Lett., 1994; Medarde et al., Bioorg. Med. Chem. Lett., 1995; Pettit et al, J. Med. Chem., 1995; Wood et al, Br. J. Cancer., 1995; Bedford et al, Bioorg. Med. Chem. Lett., 1996; Dorr et al, Invest. New Drugs, 1996; Jonnalagadda et al., Bioorg. Med. Chem. Lett., 1996; Shirai et al, Heterocycles, 1997; Aleksandrzak K, Anticancer Drugs, 1998; Chen et al, Biochem. Pharmacol., 1998; Ducki et al, Bioorg. Med. Chem. Lett., 1998; Hatanaka et al, Bioorg. Med. Chem. Lett., 1998; Medarde, Eur. J. Med. Chem., 1998; Medina et al, Bioorg. Med. Chem. Lett., 1998; Ohsumi et al, Bioorg. Med. Chem. Lett., 1998; Ohsumi et al., J. Med. Chem., 1998; Pettit G R et al., J. Med. Chem., 1998; Shirai et al, Bioorg. Med. Chem. Lett., 1998; Banwell et al, Aust. J. Chem., 1999; Medarde et al, Bioorg. Med. Chem. Lett., 1999; Shan et al, PNAS, 1999; Combeau et al, Mol. Pharmacol, 2000; Pettit et al, J. Med Chem, 2000; Pettit et al, Anticancer Drug Design, 2000; Pinney et al, Bioorg. Med. Chem. Lett., 2000; Flynn et al., Bioorg. Med. Chem. Lett., 2001; Gwaltney et al, Bioorg. Med. Chem. Lett., 2001; Lawrence et al, 2001; Nguyen-Hai et al, Bioorg. Med. Chem. Lett., 2001; Xia et al, J. Med. Chem., 2001; Tahir et al., Cancer Res., 2001; Wu-Wong et al., Cancer Res., 2001; Janik et al, Bioorg. Med. Chem. Lett., 2002; Kim et al., Bioorg Med Chem. Lett., 2002; Li et al, Bioorg. Med. Chem. Lett., 2002; Nam et al, Bioorg. Med. Chem. Lett., 2002; Wang et al, J. Med. Chem. 2002; Hsieh et al, Bioorg. Med. Chem. Lett., 2003; Hadimani et al., Bioorg. Med. Chem. Lett., 2003; Mu et al, J. Med. Chem., 2003; Pettit et al, J. Med. Chem., 2003; WO 02/50007, WO 02/22626, WO 02/14329, WO 99/51246, WO 99/34788, WO 99/35150, WO 99/48495, WO 92/16486, WO 01/12579, WO 01/09103, WO 01/81355, WO 01/81288, WO 01/84929, WO 00/35865, WO 00/73264, WO 00/06556, WO 00/48590, WO 00/48591, WO 00/48590, U.S. Pat. Nos. 6,433,012, 6,201,001, 6,150,407, 6,169,104, 5,731,353, 5,674,906, 5,569,786, 5,561,122, 5,430,062, 5,409,953, 5,525,632, 4,996,237 and 4,940,726 and U.S. patent application Ser. No. 10/281,528, the entire disclosures of which are incorporated herein by reference.

Other tubulin binding agents administered as VTAs include the following agents or their prodrugs: 2,3-disubstituted Benzo[b]thiophenes (U.S. Pat. Nos. 5,886,025; 6,162,930, and 6,350,777), 2,3-disubstituted benzo[b]furans (WO 98/39323), 2-3-disubstituted indoles (WO01/19794), disubstituted dihydronaphthalenes (WO 01/68654), Colchicine analogs (WO 99/02166), the entire disclosures are incorporated by reference herein. Finally, additional non-cytotoxic prodrugs of tubulin binding agents, which are converted to a substantially cytotoxic drug by action of an endothelial enzyme are disclosed in WO 00/48606, which is incorporated by reference here.

The invention is not limited to the treatment of tumors or cancer, and includes other, non-malignant diseases that are characterized by the presence of vascular proliferation. Vascular Proliferation disorders include those of the eye such as Macular Degeneration and Diabetic Retinopathy. CA4P and other tubulin binding agents have been described in WO 03/006002 and US2003/0092774 for the treatment of these and other diseases that are characterized by neovascularization and are incorporated in their entirety herein.

"Cancer", "Neoplastic Disease", and "Tumor" when used herein shall be used interchangeably and shall refer to the abnormal presence of cells which exhibit relatively autonomous growth, so that they exhibit an aberrant growth phenotype characterized by a significant loss of cell proliferation control. Cancerous cells can be benign or malignant. In various embodiments, the cancer affects cells of the bladder, blood, brain, breast, colon, digestive tract, lung, ovaries, pancreas, prostate gland, thyroid, or skin.

a) solid carcinomas, including cancers of the lung (such as small cell lung cancer, non-small cell lung cancer, and lung adenocarcinoma), colon (including colorectal cancer), ovaries, prostrate, testes, cervix, genitourinary tract, bladder (including accelerated and metastatic bladder cancer), liver, larynx, esophagus, stomach, breast, kidney, gall bladder, thyroid, pancreas (including exocrine pancreatic carcinoma), and skin (including squamous cell carcinoma);
b) hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burkett's lymphoma;
c) hematopoietic tumors of myeloid lineage, including acute and chronic myelogenous leukemias, myelodysplastic syndrome, and promyelocytic leukemia;
d) tumors of mesenchymal origin, including fibrosarcoma, osteosarcoma and rhabdomyosarcoma;
e) tumors of the central and peripheral nervous system, including astrocytoma, neuroblastoma, glioma and schwannomas; and
f) other tumors, including melanoma, seminoma, teratocarcinoma, osteosarcoma, xenoderoma pigmentosum, keratoacanthoma, thyroid follicular cancer, medullary thyroid cancer, anaplastic thyroid cancer, teratocarcinoma, and Kaposi's sarcoma "Effective or "Effective Amount" is an amount of a drug which generates a significant Vascular Targeting, Anti-Hypertensive, or Cardioprotective effect including but not limited to, inhibition of tumor growth or tumor growth delay, vessel regression, blood flow shutdown in proliferative vasculature, and slowing of disease progression. The methods of treatment described herein will produce an effect, as measured by, for example, one or more of: average blood pressure, the extent of the anti-tumor effect, the response rate, the time to disease progression, and the survival rate.

A "pharmaceutically acceptable salt" is substantially non-toxic and possesses the desired pharmacokinetic properties. It is palatable and soluble, and can include acids in addition to salts, such as amino acids, hydrochlorides, hydrobromides, phosphates, sulphates, hydrogen sulphates, alkylsulphonates, arylsulphonates, acetates, ascorbates, benzoates, citrates, glycolates, maleates, nitrates, fumarates, stearates, salicylates, succinates, oxalates, lactates, and tartrates; alkali metal cations such as Na, K, Li, alkali earth metal salts such as Mg or Ca; or organic bases dicyclohexylamine, tributylamine, pyridine, triethylamine, and as others disclosed in PCT International Application Nos. WO02/22626 or WO00/48606. The salts of the present invention can be synthesized by conventional chemical methods. Generally, the salts are prepared by reacting the free base or acid with stoichiometic amounts or with an excess of the desired salt-forming inorganic or organic acid or base, in a suitable solvent or solvent combination.

A "tubulin binding agent" is a ligand of tubulin or a compound capable of binding α or β-tubulin monomers, αβ-tubulin heterodimers, or polymerized microtubules, and interfering with the polymerization or depolymerization of microtubules. The tubulin binding site interactions vary between each class of Tubulin Binding Agent. Photoaffinity labeling and other binding site elucidation techniques have identified three key binding sites: 1) the Colchicine site (Floyd et al, Biochemistry, 1989; Staretz et al, J. Org. Chem., 1993; Williams et al, J. Biol. Chem., 1985; Wolff et al, Proc. Natl. Acad. Sci. U.S.A., 1991), 2) the Vinca Alkaloid site (Safa et al, Biochemistry, 1987), and 3) a site on the polymerized microtubule to which taxol binds (Rao et al, J. Natl. Cancer Inst., 1992; Lin et al, Biochemistry, 1989; Sawada et al, Bioconjugate Chem, 1993; Sawada et al, Biochem. Biophys. Res. Commun., 1991; Sawada et al, Biochem. Pharmacol., 1993).

"Transient Hypertension" is a brief increase in blood pressure or heart rate that is observed within a warm-blooded patient within the first twenty-four hours following administration of a Vascular Targeting Agent.

"Vascular proliferative disorders" include any mammalian disease state in which the pathology of the disease is characterized by the presence of endothiulium, arteries, blood vessels, or neovasculature formed by undesirable and pathological angiogenesis that is associated with disease states other than malignant diseases such as cancer, including without limitation ocular diseases such as wet or age-related macular degeneration, diabetic retinopathy, retinopathy of prematurity, diabetic molecular edema, uveitis, and corneal neovascularization, and other disease states including psoriasis, rheumatoid arthritis, atheroma, restenosis, Kaposi's sarcoma, haemangioma, and, in general, inflammatory diseases characterized by vascular proliferation.

"Vascular targeting" or "vascular shutdown" refers to the selective destruction, damage, or occlusion, whether reversible or irreversible, partial or incomplete, of existing or established microvessels. In a preferred embodiment, the selective destruction, damage, or occlusion of microvessels is reversible.

Pharmaceutical compositions of the invention are formulated to be compatible with its intended route of administration. Pharmaceutical compositions are prepared from the active ingredients or their salts in combination with pharmaceutically acceptable carriers.

As with the use of other chemotherapeutic drugs, the individual patient will be monitored in a manner deemed appropriate by the treating physician. Dosages can also be reduced if severe neutropenia or severe peripheral neuropathy occurs, or if a grade 2 or higher level of mucositis is observed, using the Common Toxicity Criteria of the National Cancer Institute.

The compositions of the present invention are formulated for systemic administration. Examples of systemic routes of administration include parenteral, e.g., intravenous, intradermal, subcutaneous, oral (e.g., inhalation), transmucosal, and rectal administration. Solutions or suspensions used for parenteral or subcutaneous application include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH is adjusted with acids or bases, such as hydrochloric acid or sodium hydroxide. The parenteral preparation is enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions are prepared by incorporating the active compound (e.g., a vascular targeting agent) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound is incorporated with excipients and used in the form of tablets, troches, or capsules. Oral compositions are prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressured container or dispenser which contains a suitable propellant, e.g., a gas such as carbon dioxide, or a nebulizer.

Systemic administration can also be transmucosal or transdermal. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In addition to the vascular targeting agents described above, the invention also includes the use of pharmaceutical compositions and formulations comprising a vascular targeting agent in association with a pharmaceutically acceptable carrier, diluent, or excipient, such as for example, but not limited to, water, glucose, lactose, hydroxypropyl methylcellulose, as well as other pharmaceutically acceptable carriers, diluents or excipients generally known in the art.

It is intended that the systemic and non-systemic administration of VTAs and tubulin binding agents in accordance with the present invention will be formulated for administration to mammals, particularly humans. However, the invention is not limited in this respect and formulations may be prepared according to veterinary guidelines for administration to animals as well.

The invention is further illustrated by the following non-limiting examples and with reference to the accompanying figures. All examples outline experiments performed in animal models and should in no way be construed as limiting the scope of the invention to these animals. In a human clinical setting non-invasive methods for measuring blood pressure would be used. For example, a simple arm cuff or sphygmomanometer measure blood pressure directly using the oscillometric method or connected to a pulse transducer for continuous measurement.

EXAMPLE 1

Control of Blood Pressure in VTA-Treated Rats

Healthy male BD9 rats were anaesthetized approximately 30 minutes before testing to allow for implantation of diagnostic catheters. Rats were under continuous anaesthetization for the course of the experiment by intraperitoneal administration of a mixture of fentanyl-fluanosine (Hypnorm, Janssen Animal Health, High Wycombe, UK) and midolozam (Hypnovel, Roche Products Ltd., Welwyn Garden City, UK). A tail vein and a tail artery were cannulated using non-sterile Portex fine bore polythene catheters (external diameter 0.96 mm, internal diameter 0.58 mm, Portex Ltd., Hythe, Kent, UK MABP was continuously monitored directly via the arterial cannula using a Model P23XL pressure transducer (Spectramed Inc, Critical Care Division, Oxnard, Calif.) connected to chart recorder and custom software was used to calculate the average arterial blood pressure.

The vascular targeting agent CA-4DP (OXiGENE Inc, Watertown, Mass.) was dissolved in 0.9% saline to which a few drops of 5% $Na_2CO_3$ was added to adjust the pH to aid dissolution, and was administered by intraperitoneal injection ("ip") at 30 mg/kg or 10 mg/kg in an injection volume of 3 ml/kg. Control animals received drug vehicle only.

Figure 1:
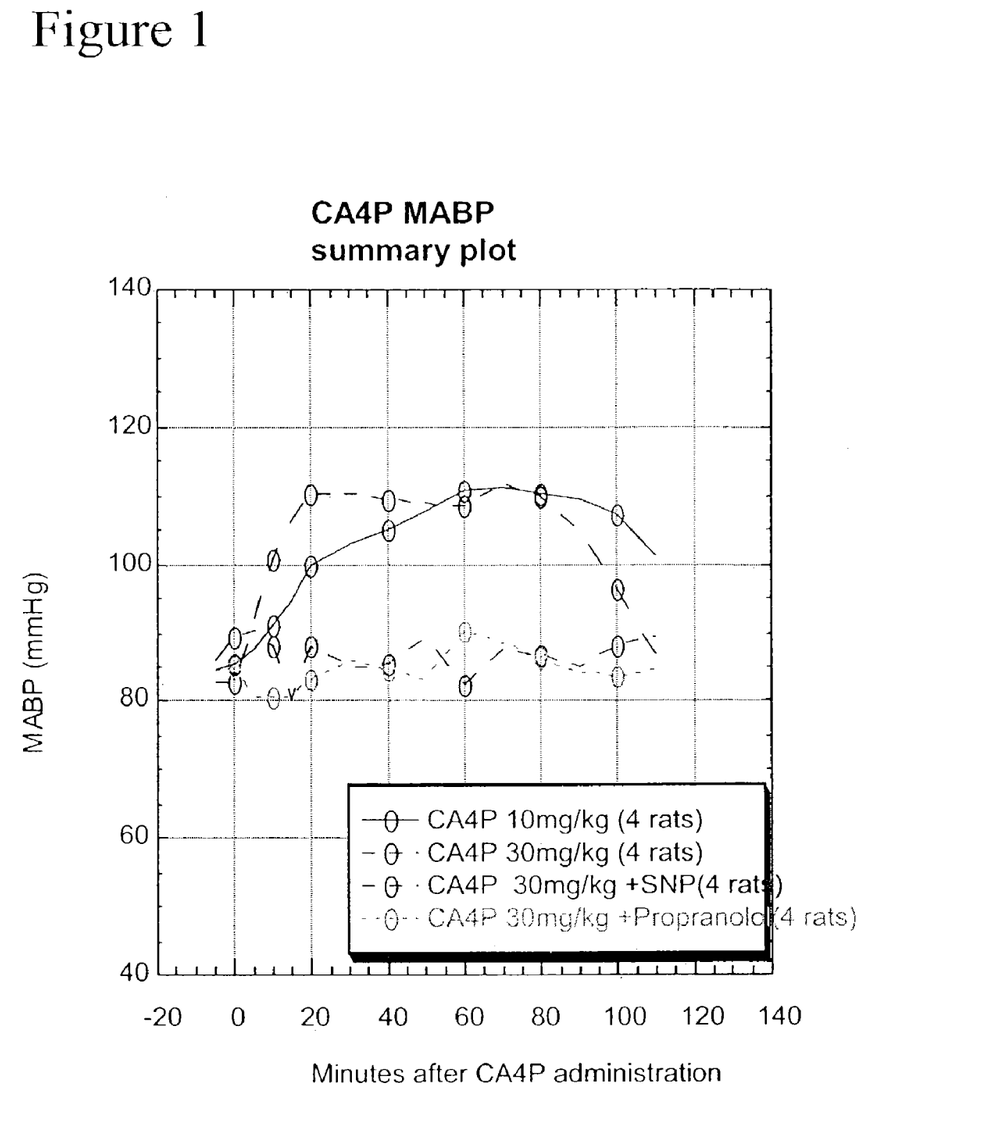
FIG. 1 is a graph of the effect of CA-4DP treatment on the average MABP of individually treated animals.

FIG. 1 demonstrates the effect of CA-4DP treatment on the average MABP of individually treated animals. Prior to treatment with CA-4DP, MABP was 84.1 mmHg (8 rats). Within 20 minutes of administering 30 mg/kg CA-4DP alone (4 rats), MABP rose to 110.3 mmHg and stabilized for approximately an hour before falling back to pre-treatment levels. A lower dose of CA-4DP (10 mg/kg in 4 rats) caused a less acute and more gradual increase in MABP, eventually reaching similar levels (110.7 mmHg) within 1 hr of treatment. MABP was stabilized at 110 mmHg for 40 minutes before falling back down to control levels.

In a separate group of rats (n=4), the beta blocker DL-propranolol (1-[ispropylamino]3-[1-napthyloxy]-2-propanol hydrocholoride; Sigma-Aldrich Co., St. Louis Miss.) was administered by continual i.v. infusion into the venal cannula at rate of 20 ug/kg/min. As demonstrated in FIG. 1, the infusion of propranolol just prior to dosing with 30 mg/kg CA-4P prevented the dramatic increase in blood pressure seen in CA-4DP-treated rats. Instead, MABP was stabilized within 5-10 mmHg of control levels and maintained at that level for the course of 2 hours. Saline control alone had no effect on controlling CA-4DP-induced increase in MABP (data not shown).

In contrast to propranolol treatment, the vasodilator Sodium Nitroprusside Dihydrate ("SNP", sodium nitroferricyanide; Sigma-Aldrich Co., St. Louis, Miss.) was administered subsequent to CA-4DP treatment (30 mg/kg). SNP was infused (20 ug/kg/min) at the first sign of an increase in MABP. As FIG. 1 again demonstrates, this led to prolonged stabilization of MABP, similar to that observed with propranolol. When the infusion was stopped, however, MABP rose sharply in all treated rats.

EXAMPLE 2

Effect of Antihypertensive Agents on Blood Flow in Tumor-Bearing, VTA-Treated Rats To investigate the in vivo effects of single-dose CA-4DP and anti-hypertensives on tumor haemodynamics, P22 rat carcinosarcoma cells were implanted in the left flank of 7-9 week old BD9 rats and grown for 2-3 weeks to allow for tumor establishment. Tumors were used for experimentation when the geometric mean tumor diameter reached 12-16 mm (approximately 2-3 weeks post-implantation).

Tumor blood flow ("THF") measurements were made with the radioactive tracer Iodoantipyrine ($^{125}$I-IAP, Institute for Cancer Research, Sutton, UK). IAP is readily diffusible agent, and accumulates in tissues in direct proportion to blood supply. Methods for using this tracer have been described in detail previously (Tozer G M and Shaffi K M, British Journal of Cancer, 1993. 67(5):981-8, incorporated by reference herein). Rats were anaesthetized and cannulated as in Example 1, except an additional tail vein was cannulated to permit intravenous infusion of the radioactive tracer. Animals were also heparinised 10 minutes prior to blood flow measurement with 100 units of heparin in a 100 ul volume (Monoparin, CP Pharmaceuticals LTD, Wrexham, UK) in order to avoid any of the potential procoagulant effects of CA-4DP.

As in Example 1, MABP was continuously monitored via the tail artery cannula following dosing with CA-4DP (i.p., 30 mg/kg) or Saline. Separate treatment groups were infused with SNP, propranolol, or saline. Propranolol was administered before CA-4DP treatment while SNP infusions were started only when the MABP began to rise in CA-4DP-treated rats.

Approximately 1 hour after CA-4DP dosing, THF measurements were initiated by infusing 0.3 MBq (8 uCi) of the radioactive tracer into the tail vein catheter for 30 seconds, at a rate of 1.6 ml/min. During this 30 second period, free-flowing arterial blood was collected from one of the arterial cannulas into pre-weighed vials at 1 second intervals. Promptly at the end of the 30 second infusion, the rat was killed by i.v. injection of Euthatal (Rhone Merieux Ltd., Harlow, UK) and the tumor and was immediately excised. Blood and tissue samples were weighed and counted on a Wallac Autogamma well counter.

Absolute blood flow to the tumor was calculated from the tissue counts, the arterial input function derived from the arterial blood counts for each individual animal, and the previously determined equilibrium partition coefficient for IAP in tumor tissue. This method is based on principles derived by Kety (Methods Med. Res., 1960, 8: 223-227) and is described elsewhere (Tozer et al., 1994. Br. J. Cancer, 70: 1040-1046). Both references are incorporated by reference herein.

Figure 2A:
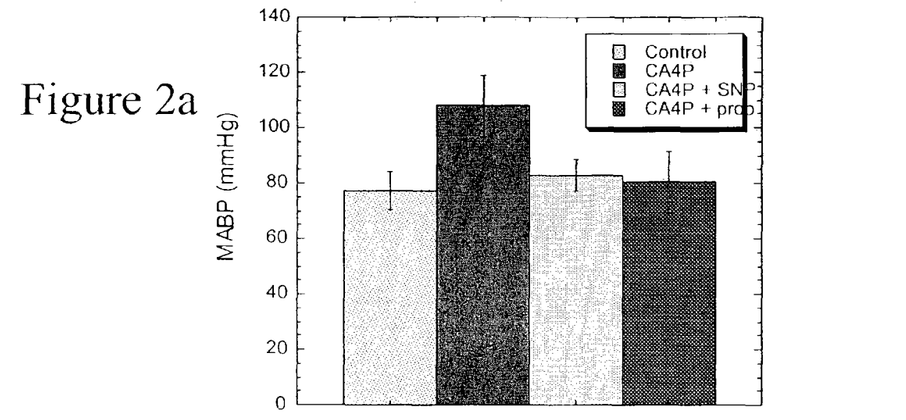
FIG. 2a is a bar graph of MABP in each treatment group 1 hour after CA-4DP or control dosing and just prior to THF assay.

FIG. 2a illustrates the MABP in each treatment group 1 hour after CA-4DP or control dosing and just prior to THF assay. CA-4DP increased MABP 72% from 7.2 mmHg in control animals (n=6 animals) to 107.9 mmHg. Co-administration of SNP (n=6) or propranolol (n=5) reduced MABP to Saline control levels (82.7 and 80.2 mmHg respectively). As in the previous example, MABP after CA-4DP alone is significantly higher than for any other group. Heart Rate was also measured in treated animals at 1 hour post-CA-4DP dosing. This value was calculated from the peak frequency from the MABP measurements. FIG. 2c demonstrates that Heart Rate was significantly reduced in CA-4DP-treated rats (265.6 bpm, n=5) relative to saline control and this effect was also observed with co-administration of propranolol (248.5 bpm, n=5). However, SNP removed this effect and returned the heart rate to normal levels (414.4 bpm, n=5).

Figure 2B:
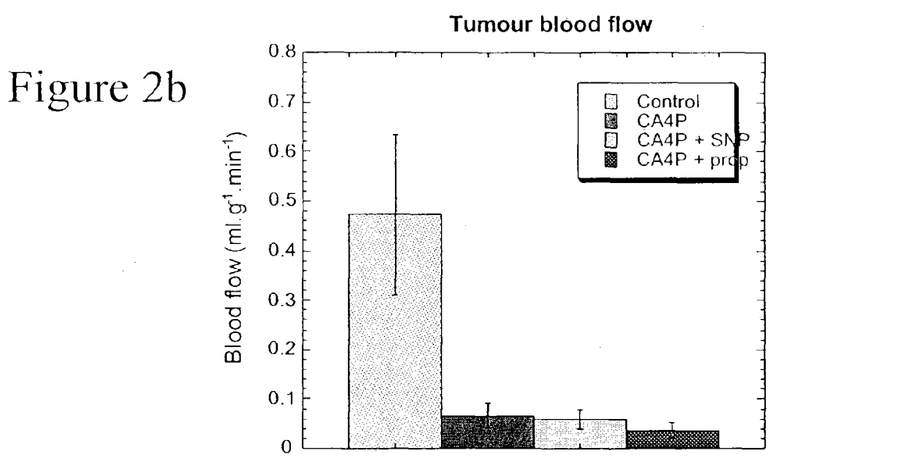
FIG. 2b is a bar graph showing that CA-4DP has dramatic effects on blood flow to tumor tissue.
Figure 2C:
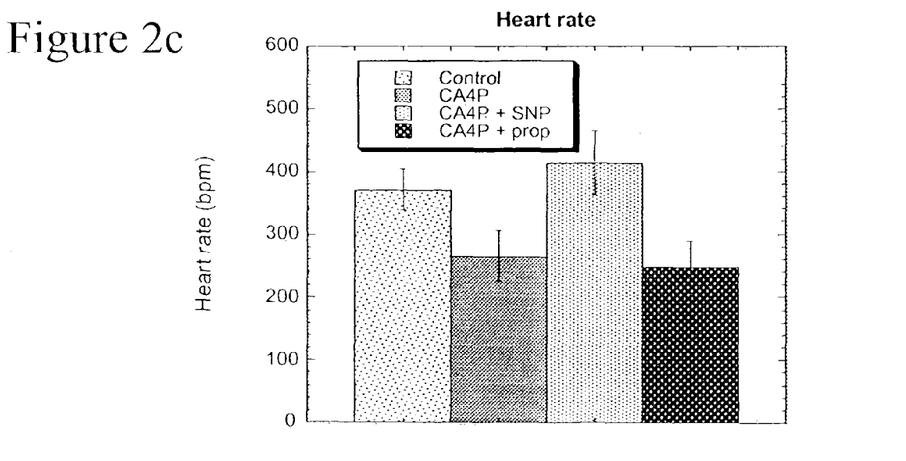
FIG. 2c is a bar graph of heart rate in each treatment group.

As FIG. 2b demonstrates, CA-4DP has dramatic effects on blood flow to tumor tissue. Co-administration of an anti-hypertensive does not significantly alter the magnitude of these effects. Approximately 1 hour after treatment, THF was reduced to 14% of saline control in rats treated with CA-4DP only, while co-administration of SNP or propranolol caused a reduction in tumor blood flow of 12.6 and 7.6% of control respectively.

EXAMPLE 3

Effect of Single Dose VTA on Heart Tissue and the Protective Effects of Propranolol To investigate the temporal effect of VTAs on heart tissue, female Harlan Sprague Dawley rats were injected i.v. with a single dose of CA-4DP (100 mg/kg) or saline control and sacrificed at different time intervals post-treatment. The Sprague Dawley rat strain was used as it is especially sensitive to the effects of CA-4DP. At the end of the experiment, cardiac tissue samples from all animals were subjected to formalin fixation and paraffin embedding for sectioning. Tissue section (6 um thick) were stained with hemotoxylin and eosin using standard procedures, and examined under light microscopy. Digital photographs were taken for each sample.

Figure 3:
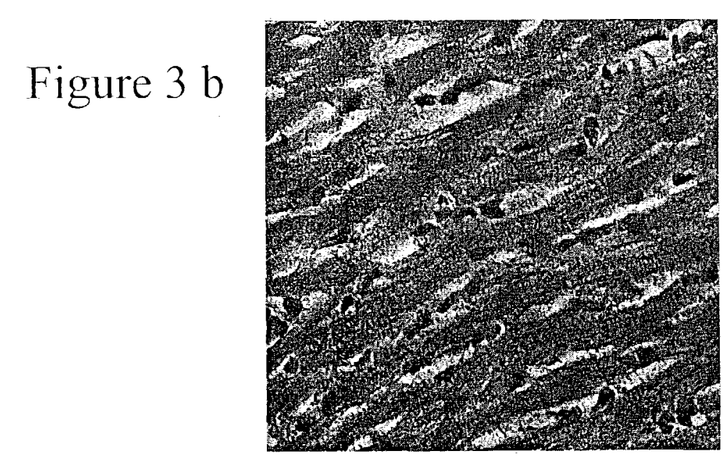
FIG. 3a is a photograph of a histological section of muscle tissue from control rats.
FIG. 3b is a photograph of a histological section of muscle tissue from rats 4 days after intravenous administration of CA-4DP at 100 mg/kg.
FIG. 3c is a photograph of a histological section of muscle tissue from rats 4 days after intravenous administration of CA-4DP at 100 mg/kg where the rats were pretreated with propranolol.
Figure 3A:
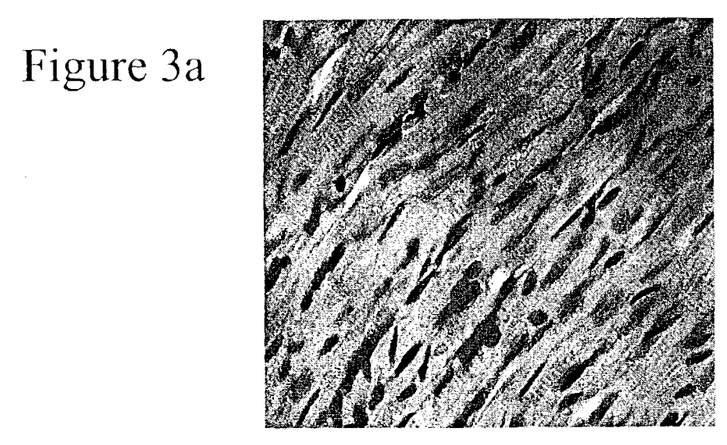

Intravenous administration of CA-4DP at 100 mg/kg induced drug-related histopathological changes in the heart manifesting necrosis and degeneration of cardiac cells in some localized areas, especially in the apical region in the septum and left ventricular free wall. At 6 hours (n=6), some blood vessels in the heart tissue were observed dilated, with increased red blood cells permeated into the nearby tissue. This resembles the early response of blood shutdown or infarction. The cell membrane was not clearly visible and some cells appeared to have pyknotic or condensed nuclei. At 24 hours, the total visible mycardiac cell numbers were further decreased. Inflammation cells infiltrated the heart tissue. Myocardial fibers were irregular and wavy and local necrosis was found in some cases. At 4 days (n=6), myofiber was characterized by loss of striation, fragmentation, a manifestation of necrosis and degeneration. This pathology is clearly visible in FIG. 3b which presents a representative tissue sample at 1 OOX magnification. These results contrast with those for control rats treated for the same 4 day period, in which case muscle tissue appeared perfectly healthy and well-defined muscle cell nuclei and intact endothelia were clearly distinguishable (FIG. 3a, 100× magnification).

Figure 3C:
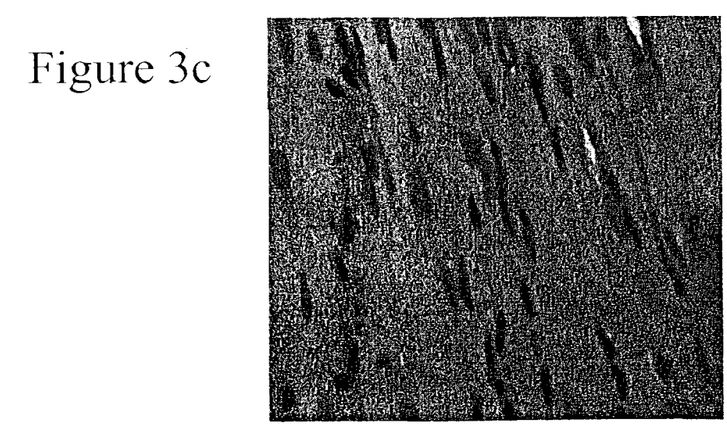

To investigate the cardiac protective properties of an antihypertensive agent, another group of rats (n=6) were pretreated with 2 mg/kg Propranolol Hydrochloride (INDERAL®, Wyeth-Ayerst, Philadelphia, Pa.) at 1 hour prior to administration of CA-4DP (100 mg/kg). With pretreatment of propranolol, the adverse effects of propranolol were observed to be minimized, with less or no hyalinization in the myocytes. There was no abnormal CA-4DP-related histopathology at either 6 or 24 hours post-treatment and no evidence of an increase in total number of visible myocardial cells, no evidence of neutrophil or macrophage infiltration, necrosis, or abnormal myofibers. FIG. 3c demonstrates that cardiac tissue remained healthy even after 4 days of CA-4DP treatment. These observations are consistent with a cardioprotective effect of anti-hypertensive agents which counteracts any cardiotoxic side effects of vascular targeting agents.

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating cardiotoxicity and hypertension induced by a vascular targeting agent, comprising administering said vascular targeting agent in combination with an anti-hypertensive agent to a mammal, wherein said vascular targeting agent is selected from the group consisting of a combretastatin, combretastatin A-4 phosphate, a combretastatin A-1 diphosphate, or a pharmaceutically acceptable salt thereof and further wherein said anti-hypertensive agent is a vasodilator selected from the group consisting of isosobide mononitrate, isosorbide dinitrate, nitroglycerin, fenoldopam mesylate, epoprostenol sodium, milrinone lactate, and sodium nitroprusside.

2. The method of claim 1, wherein said vascular targeting agent is selected from the group consisting of Combretastatin A-4 Phosphate, Combretastatin A-1 Diphosphate, and a pharmaceutically acceptable salt thereof.

3. The method of claim 1, wherein said vasodilator is nitroglycerin.

4. The method of claim 1, wherein said pharmaceutically acceptable salt is a sodium salt or a triethylamine salt.

5. The method of claim 1, wherein said vascular targeting agent is combretastatin A-4 disodium phosphate.

6. The method of claim 1, wherein said vascular targeting agent is combretastatin A-1 tetrasodium diphosphate.

7. The method of claim 6, wherein said antihypertensive agent is nitroglycerin.

8. The method of claim 1, wherein said vascular targeting agent or a pharmaceutically acceptable salt thereof, is administered at a dosage of 100 mg/kg or less.

9. The method of claim 1, wherein said vascular targeting agent or a pharmaceutically acceptable salt thereof is administered intravenously.

10. The method of claim 1, wherein said anti-hypertensive agent is administered simultaneously with said vascular targeting agent.

11. The method of claim 1, wherein said anti-hypertensive agent is administered prior to the administration of said vascular targeting agent.

12. The method of claim 1, wherein said anti-hypertensive agent is administered following the administration of said vascular targeting agent.

13. The method of claim 1, wherein said vascular targeting agent is being chronically administered to said animal.

* * * * *